United States Patent
Roeder et al.

(10) Patent No.: US 9,498,361 B2
(45) Date of Patent: Nov. 22, 2016

(54) REPOSITIONABLE DIAMETER CONSTRAINTS

(71) Applicant: Cook Medical Technologies LLC, Bloomington, IN (US)

(72) Inventors: Blayne A. Roeder, Bloomington, IN (US); Krasnodar Ivancev, London (GB)

(73) Assignee: Cook Medical Technologies LLC, Bloomington, IN (US)

( * ) Notice: Subject to any disclaimer, the term of this patent is extended or adjusted under 35 U.S.C. 154(b) by 258 days.

(21) Appl. No.: 14/132,903

(22) Filed: Dec. 18, 2013

(65) Prior Publication Data

US 2014/0172069 A1 Jun. 19, 2014

Related U.S. Application Data

(60) Provisional application No. 61/739,240, filed on Dec. 19, 2012.

(51) Int. Cl.
*A61F 2/06* (2013.01)
*A61F 2/95* (2013.01)
*A61F 2/07* (2013.01)

(52) U.S. Cl.
CPC . *A61F 2/95* (2013.01); *A61F 2/07* (2013.01); *A61F 2002/075* (2013.01); *A61F 2002/9511* (2013.01); *A61F 2002/9534* (2013.01); *A61F 2250/001* (2013.01)

(58) Field of Classification Search
CPC .... A61F 2/07; A61F 2/95; A61F 2002/9511; A61F 2/06
See application file for complete search history.

(56) References Cited

U.S. PATENT DOCUMENTS

| | | | |
|---|---|---|---|
| 2011/0125244 A1 | 5/2011 | Roeder et al. | |
| 2012/0172965 A1* | 7/2012 | Kratzberg | A61F 2/962 623/1.12 |

* cited by examiner

*Primary Examiner* — Victor Nguyen
(74) *Attorney, Agent, or Firm* — Brinks Gilson & Lione

(57) ABSTRACT

An endoluminal prosthesis includes an expandable stent graft that includes a cannula extending through a lumen of the stent graft. A suture is threaded along the perimeter of the graft through openings therein, with an inner end of the suture mounted to the cannula. The cannula is rotatable relative to the graft to wind or unwind the suture around the cannula and cause the graft to become compressed when wound or allow the graft to expand when unwound. The cannula includes an attachment member for retaining an inner end of the suture, and the attachment member can release the inner end of the suture when adjustment of the graft diameter is no longer desired.

20 Claims, 4 Drawing Sheets

REPOSITIONABLE DIAMETER CONSTRAINTS

CROSS-REFERENCE TO RELATED APPLICATIONS

This application claims the benefit of U.S. Provisional Application No. 61/739,240, filed Dec. 19, 2012, which is hereby incorporated by reference in its entirety herein.

BACKGROUND

1. Field of the Invention

The present embodiments relate generally to a delivery system for an endoluminal prosthesis having an expandable graft.

2. Description of Related Art

Using stent grafts to treat aneurysms or similar defects is common in the medical field. Stent grafts are deployed by accessing a vasculature with a small incision in the skin and guiding a delivery system to the target area. This intraluminal delivery is less invasive and generally preferred over more intrusive forms of surgery.

The stent grant can be placed against the vessel wall in the area of the defect to close off the defect and provide patent fluid flow through the area of the defect, thereby allowing the defect to heal itself while limiting or substantially preventing blood loss through the vessel wall.

Methods for delivering a stent graft are well known in the art, and involve guiding the stent graft over a guide wire or similar structure until the graft reaches the target location. During the delivery, the stent graft, including a cannula therein, is in a compressed state with a diameter that is smaller than the diameter of the graft in the deployed state. The smaller diameter allows the graft to be delivered while limiting the trauma to the patient, with the graft typically delivered through the use of a catheter, as is known in the art.

Once the catheter with the graft is delivered to the target site, the catheter can be withdrawn back along the guide wire toward the surgeon, leaving the graft in place. The stent is then released from its compressed state by typically withdrawing a trigger wire in the case of a self-expanding stent. After withdrawing the trigger wire, the self-expanding stent will expand outwardly into contact with the luminal wall.

Alternatively, the stent can be expanded by using a balloon therein, which can be inflated to force the diameter of the stent outward and into engagement with the luminal wall.

Once expanded, the stent is generally limited in its ability to reduce the diameter. This is because the purpose of the stent is to provide outward pressure on the luminal wall to remain in place and treat the vascular defect.

However, there are instances where the surgeon may desire the ability to reduce the diameter of the stent after it has at least partially expanded, such as an instance where the stent needs to be repositioned along the vasculature, either due to initial misplacement or discovery of an additional defect adjacent the target site.

In the event the stent graft is not adequately positioned, the surgeon may be required to deliver an additional stent graft to the same target area to sufficiently treat the defect, adding time and material to the procedure and resulting in increased trauma to the patient.

Therefore, there is a need to provide a stent graft that can be at least partially expanded and subsequently compressed to allow the surgeon to reposition the stent graft after initial expansion.

SUMMARY

The present embodiments provide a system for delivering an endoluminal prosthesis and methods for facilitating deployment of the endoluminal prosthesis. In one example, a system for deploying an endoluminal prosthesis is provided, the system comprising: a graft comprising biocompatible material having at least one lumen extending therethrough; a rotatable cannula extending at least partially through the graft lumen; a suture having a first portion and a second portion, the first portion being coupled to the rotatable cannula within the graft lumen and the second portion being coupled to the graft, wherein the lengths of the first and second portions adjust in response to rotation of the rotatable cannula to vary the diameter of the graft.

In one form, the graft has a first diameter in response to rotation of the cannula in a first direction, the graft has a second diameter larger than the first diameter in response to additional rotation of the cannula in the first direction, and the graft has a third diameter less than the second diameter in response to rotation of the cannula in a direction opposite the first direction.

In another form, the suture is at least partially wound around the cannula within the graft lumen.

In another form, the graft comprises a plurality of openings therethrough, the suture first portion is at least partially threaded through the plurality of openings, and alternating portions of the suture first portion are disposed inside and outside of the graft.

In another form, the suture includes a loop portion at the first end thereof, the cannula has an attachment member thereof, and the loop portion is coupled to the attachment member.

In another form, the attachment member comprises a hook protruding radially from the cannula.

In another form, the attachment member comprises a wire extending longitudinally along the cannula.

In another form, the cannula has a tubular body with a lumen extending therethrough and first and second longitudinally spaced openings in the body, the wire extends through the lumen, through the first opening, and through second opening, an intermediate portion of the wire is disposed outside the cannula, and the intermediate portion extends through the suture loop.

In one example, a method for delivering an endoluminal prosthesis comprises the steps of: locating, within a patient's body, an endoluminal prosthesis having a graft comprising biocompatible material having at least one lumen extending therethrough, wherein a cannula extends at least partially through the graft lumen and a suture is at least partially wound about the cannula and at least partially mounted about a perimeter of the graft; rotating the cannula in a first direction; in response to rotating the cannula in a first direction, unwinding a portion of the suture; expanding the graft outwardly; rotating the cannula in a second direction that is opposite the first direction; in response to rotating the cannula in the second direction, winding a portion of the suture about the cannula; and reducing the diameter of the graft.

In another form, the graft includes a plurality of laterally spaced openings in the graft, the suture extends through the openings in an alternating fashion, a first portion of the suture extending about the graft is outside the graft, and a second portion of the suture extending about the graft is inside the graft.

In another form, the cannula includes an attachment member and an inner end of the suture is releasably mounted to the attachment member.

In another form, the inner end of the suture includes a loop portion and the attachment member extends through the loop portion.

In another form, the attachment member comprises a hook fixedly mounted to the cannula.

In another form, the method further comprises the step of further rotating the cannula in the first direction and releasing the inner end of the suture from the hook.

In another form, the attachment member comprises a wire extending along the cannula and through the loop portion.

In another form, the method further comprises the step of withdrawing the wire away from the suture and out of engagement with the loop portion.

In another form, the cannula includes a lumen extending therealong, the cannula includes a pair of longitudinally aligned openings through a surface of the cannula, and the wire extends within the cannula lumen through one of the openings to the outside of the cannula and through the other opening to the cannula lumen, an intermediate portion of the wire is outside the cannula, and the intermediate portion extends through the suture loop.

In another example, a system for deploying an endoluminal prosthesis comprises: a graft comprising biocompatible material having at least one lumen extending therethrough; a rotatable cannula extending at least partially through the graft lumen; and a suture having a first portion and a second portion, the first portion being wound around the rotatable cannula within the graft lumen and the second portion extending along the perimeter of the graft, wherein the lengths of the first and second portions adjust in response to rotation of the cannula.

In another form, the system further comprises a stent coupled to the graft.

In another form, the stent comprises a self-expanding stent.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

DETAILED DESCRIPTION

Figure 1:
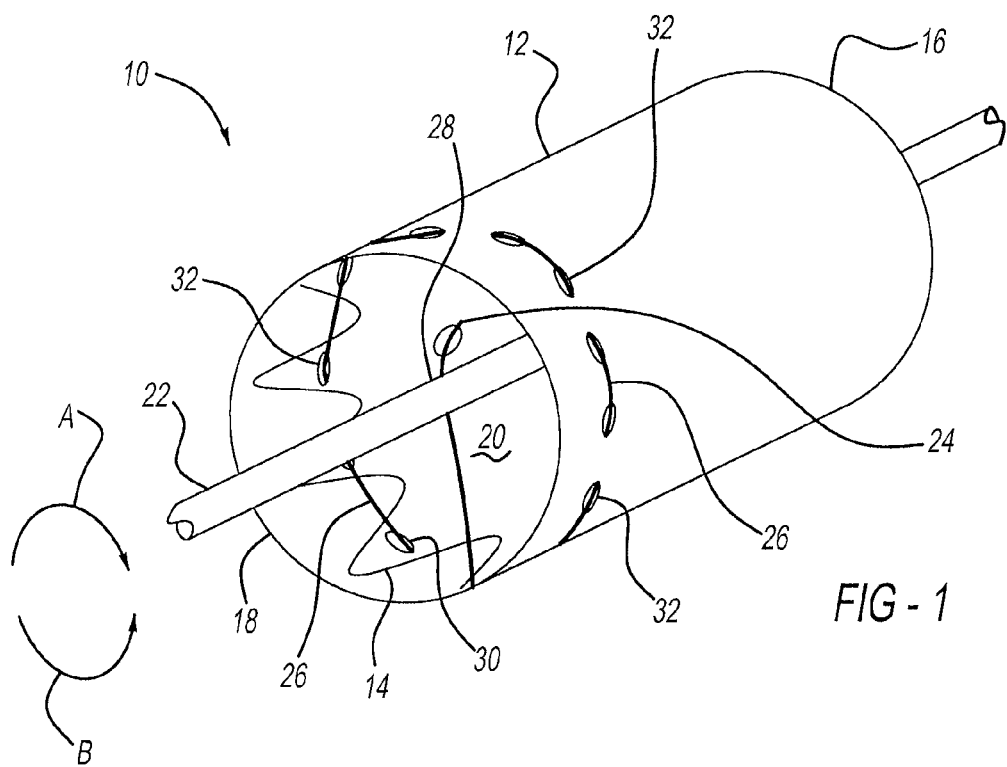
FIG. 1 is an isometric view illustrating a delivery system for deploying a stent graft with the stent graft in an expanded condition.
Figure 2:
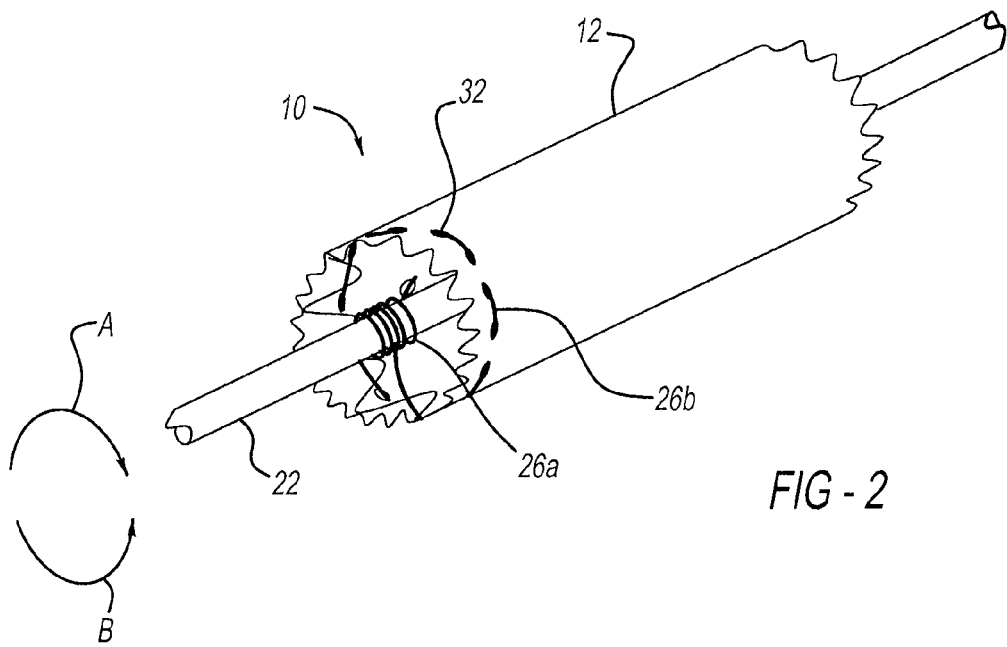
FIG. 2 is an isometric view illustrating the delivery system with the stent graft in a reduced diameter condition.

Referring now to the drawings, FIG. 1 illustrates a system 10 for delivering an endoluminal prosthesis or tubular graft 12, which can be made from any of the currently available graft materials or other biocompatible materials known in the art. The graft 12 preferably has a compressed diameter in the range of 5-8 mm, and an expanded diameter in the range of 20-46 mm. The graft 12 is shown in an expanded state in FIG. 1, but it will be appreciated that the diameter can decrease, as further described below. Of course, the above listed dimensions can vary depending on the patient or the location in the vasculature where the graft 12 is to be deployed.

The system 10 further includes a stent 14 coupled to the graft 12 and having an expandable structure known in the art. One example of the stent 14 structure can be found in U.S. patent application Ser. No. 12/945,097, filed Nov. 12, 2010, which is hereby incorporated by reference in its entirety. The stent 14 can be either self-expanding, where the stent 14 can be compressed and will spring out in response to releasing the compressing force, or balloon expandable, where a balloon (not shown) can be inflated within the stent 14 to expand the stent 14 outward to an expanded state. In one approach, the stent 14 can be in the form of one or more stent rings (not shown) disposed on either the inside of the graft 12 or the outside of the graft 12. A portion of the stent rings can be bare stents that extend beyond one or both ends of the graft 12, with the bare stents having rounded apices. The stent rings can be conventional zigzag stent rings with pointed apices, or they can have rounded apices. Alternatively, the stent rings could have other suitable stent ring designs. The stent rings are preferably sutured to the graft 12 but can also be connected to the graft 12 by any other suitable means. The stent 14 can also be in the form of a unitary self-expanding structure. These types of stent 14 structure and pre-loaded forces are well known in the art and will not be discussed in further detail. In both structure types, the stent 14 can be compressed or expanded in response to sufficient compression or expansion forces acting thereon. For purposes of discussion, when referring to expansion generally, either self-expansion or balloon expansion methods can be used.

The graft 12 includes a distal end 16, a proximal end 18, and a lumen 20 extending therebetween.

The system 10 can further include a cannula 22 extending generally along a longitudinal axis of the graft 12 and at least partially through the lumen 20. The cannula 22 can have a generally elongated shape with a relatively small diameter for facilitating insertion into a patient's vasculature. In one form, the cannula 22 has a generally a circular cross-section, however other elongate shapes could also be used, such as a shape having a generally square cross-section. The cannula 22 can have a generally solid construction, or could have a hollow tubular form. The cannula 22 can include an attachment member 24 fixedly mounted to an outer surface of the cannula 22. The various types of attachment members 24 will be further described below.

The system 10 further includes a thread or suture 26 that is coupled to both the attachment member 24 of the cannula 22 and the graft 12. More specifically, an inner end 28 of the suture 26 is releasably mounted to the attachment member 24, and an outer end 30 is mounted to the graft 12.

The graft 12 includes a plurality of openings 32 through the side of the graft 12. The openings 32 are generally evenly spaced, in one embodiment, about the perimeter of the graft 12, and are generally aligned along a plane that is transverse to the longitudinal axis of the graft 12. However, in another embodiment, the openings 32 could be spaced apart in a non-uniform manner or along a plane at an oblique angle to the longitudinal axis of the graft 12. The suture 26 can be threaded through the openings 32 in an alternating fashion, so that the suture 26 extends from the lumen 20 of the graft 12, through one of the openings 32, and to the outside of the graft 12. The suture 26 will then extend about the perimeter of the graft 12 toward the opening 32 adjacent the opening 30 through which the suture 26 extended, and then pass through this opening 32 back into the lumen 20. This threading will continue about the graft 12, so that the suture 26 alternates between extending about the perimeter of the graft 12 within the lumen 20 and extending about the perimeter on the outside of the graft 12 in a generally serpentine path. When the suture 26 reaches the final unthreaded opening 32, the suture 26 will extend through that opening 32, where it is then mounted to the graft 12.

Of course, the threading pattern described above can be altered to suit the needs of the user. For example, the threading could continue through the openings 32 so that each opening 32 is threaded twice. It will be appreciated that there are myriad variations for threading the suture 26 through the openings in the graft 12. Preferably, the number of openings 32 is at least six for effective radial compression of the graft 12 as will be explained below.

The cannula 22, having the attachment member 24 fixedly mounted thereto is rotatable within the graft lumen 20 relative to the graft 12. The rotation of the cannula 22 can be controlled by the surgeon outside of the patient's body, along with the various other surgeon controlled aspects of the catheter insertion and retraction known in the art. The cannula 22 can be rotated in both a clockwise direction A and counterclockwise direction B. It will be appreciated that the terms clockwise and counterclockwise are intended to describe rotation in opposite rotary directions, and the following rotational descriptions are not dependent on any particular point of view.

In one form, the graft 12 can be radially compressed by rotating the cannula 22 in the clockwise direction A. The rotation of the cannula 22 relative to the graft 12 will cause the suture 26 to be wrapped around the perimeter of the cannula 22. Thus, the suture 26 will have both a wrapped portion 26a and a free portion 26b. As the cannula 22 is rotated, the wrapped portion 26a will increase and the free portion 26b will decrease. Because the suture 26 is threaded through the openings 32 in the graft 12, the shortening of the free portion 26b due to the wrapping will cause the diameter of the graft 12 to decrease. The graft 12 material will generally fold over itself in an accordion fashion. The rotation of the cannula 22 can continue until the graft 12 is compressed to a desired diameter. In the case of compressing the graft 12 prior to insertion into a delivery catheter, the rotation of the cannula 22 can be in addition to traditional techniques for compressing a stent graft.

It thus follows that, after compressing the graft 12 by rotation of the cannula 22 in the clockwise direction A, the graft 12 can expand if the cannula 22 is rotated in the opposite, counter-clockwise direction B. Rotating the cannula 22 in the counter-clockwise direction B allows the free portion 26b to increase, which will allow the stent graft 12 to expand, either by self-expanding or by forcing the stent 14 and graft 12 outward by balloon inflation. In one form, the cannula 22 can terminate within the lumen 20 of the graft 12 so that the balloon (not shown) can be passed through the cannula 22 or other delivery tube so that it can be inflated within the lumen 20 of the graft 12 to effect the radial expansion. Additionally or alternatively, prior to insertion into the patient, the graft 12 can be expanded manually along with the counterclockwise rotation. Of course, if the cannula 22 has not been rotated to wind the suture 26, the cannula 22 does not need to be rotated to unwind the suture 26.

As described above, the suture 26 is mounted at its inner end 26a to the cannula 22, which allows the cannula 22 to wind and unwind the suture 26 depending on the direction of rotation. The inner end 26a of the suture 26 can also be releasable from the attachment member 24 of the cannula 22 in the event that further winding to compress the graft 12 is unnecessary or not desired. An example of such a situation would be when the graft 12 has been located within the vasculature to the satisfaction of the surgeon where further repositioning is no longer desired. The manner of releasing the suture 26 from the cannula 22 depends on the structure of the attachment member 24, which will be further described below.

Figure 3:
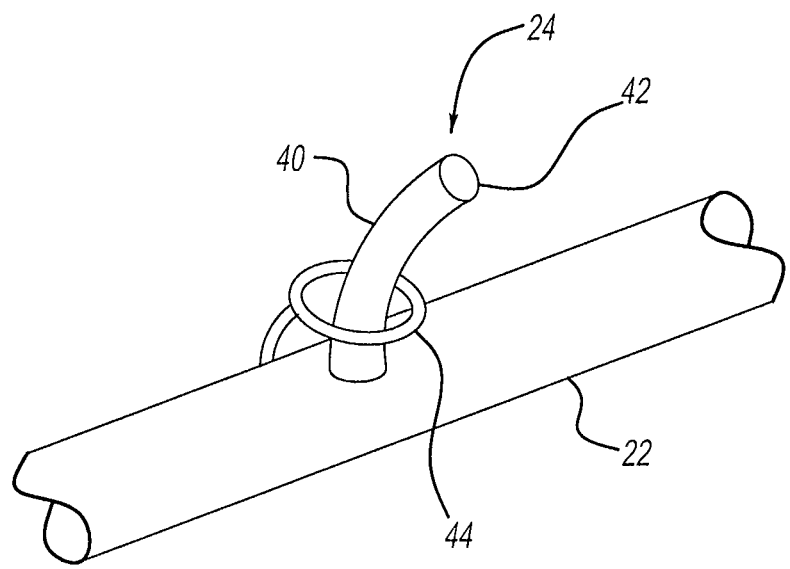
FIG. 3 is an isometric view illustrating a cannula of the delivery system having an attachment member in the form of a hook.

With reference to FIG. 3, in one form, the attachment member 24 is a hook 40 having a generally rigid and curved form. The hook 40 includes a free end 42 that is generally pointed in the direction of rotation corresponding to the rotational direction for winding the suture 26. When unwinding the suture 26, the hook 40 rotates along with the cannula 22 in the rotational direction opposite the direction that the free end 42 points. The inner end 26a of the suture can include a loop 44 that the hook 40 extends through, maintaining the connection while the cannula 22 rotates. When the cannula 22 has rotated so that the graft 12 has expanded and the suture 26 is substantially fully unwound, the curved shape of the hook 40 will cam across the loop 44 at the inner end 26a of the suture 26, causing the suture 26 to release from the cannula 22. After the release of the loop 44, further rotation of the cannula 22 will generally not result in additional winding of the suture 26 and the graft 12 will generally not undergo any additional diameter expansion. The graft 12 may expand slightly further when the suture 26 is released because the cannula is no longer limiting the graft 12 from expanding.

Figure 4:
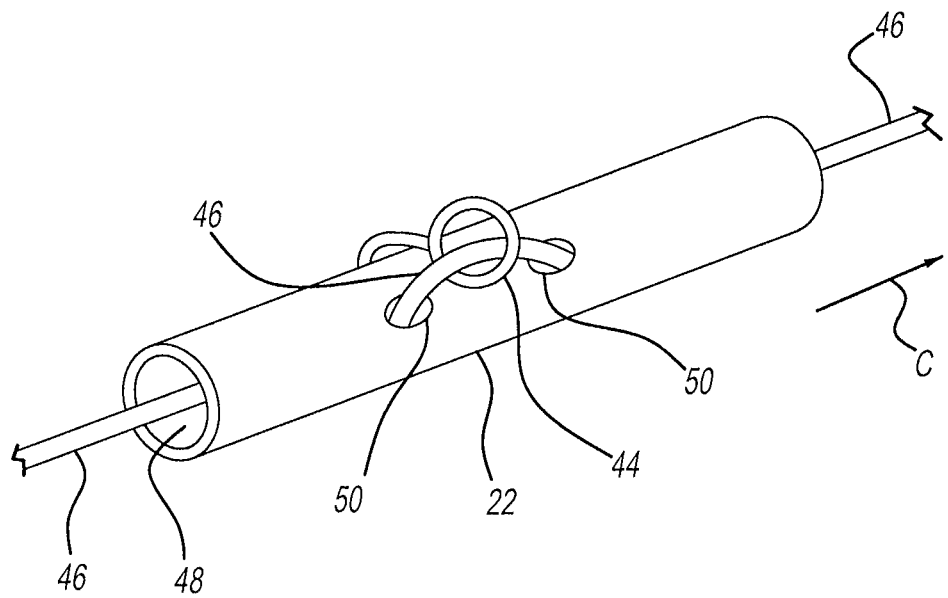
FIG. 4 is an isometric view illustrating the cannula having an attachment member in the form of a trigger wire.

With reference to FIG. 4, in another form, the attachment member 24 can be in the form of a trigger wire 46 that extends through the loop 44 at the inner end 26a of the suture 26. More specifically, the trigger wire 46 can extend through a lumen 48 of the cannula 22. The cannula 22 can include a pair of longitudinally aligned openings 50 therein, where the trigger wire 46 can extend from the lumen 48, through the opening 50 to the outside of the cannula 22. The trigger wire 46 can then pass through the loop 44 of the suture 26 and through the adjacent opening 50 back into the lumen 48. Thus, the trigger wire 46 will retain the inner end 26a of the suture 26. The cannula 22 can be rotated to wind or unwind of the suture 26 as described above. When the surgeon is satisfied with the location of the graft 12 and further diameter adjustment is no longer desired, the trigger wire 46 can be withdrawn in the direction C, thereby releasing the loop 44 of the suture 26. After the release of the loop 44, further rotation of the cannula 22 will generally not result in further adjustment of the diameter of the graft 12.

It will be appreciated that other manners of extending the trigger wire 46 through the loop 44 can be used, such as where the trigger wire 46 extends along the outside of the cannula 22 while being coupled thereto and configured to be withdrawn to release the loop 44 of the suture 26. Compared to the hook 40 of the embodiment of FIG. 3, the trigger wire 46 has the advantage of having a low radial profile without any risk of getting caught in the graft material. On the other hand, the hook 40 does not require an additional externally controlled element. Which version is preferred depends on the individual situation and on the available radial space.

Having described the general structure of the graft 12, the use of the stent graft will now be described.

As is known in the art, delivery of an endoluminal prosthesis can be performed using minimally invasive techniques, whereby a small incision is made in a patient's skin for allowing the insertion of medical devices into the patient's body.

In one approach, a guide wire 58 is inserted into the patient and guided generally toward and to the target treatment site in the body. For example, the guide wire 58 can be advanced through a patient's vasculature toward and to, for example, the ascending or descending aorta to treat an aortic aneurysm or other defect.

Figure 5:
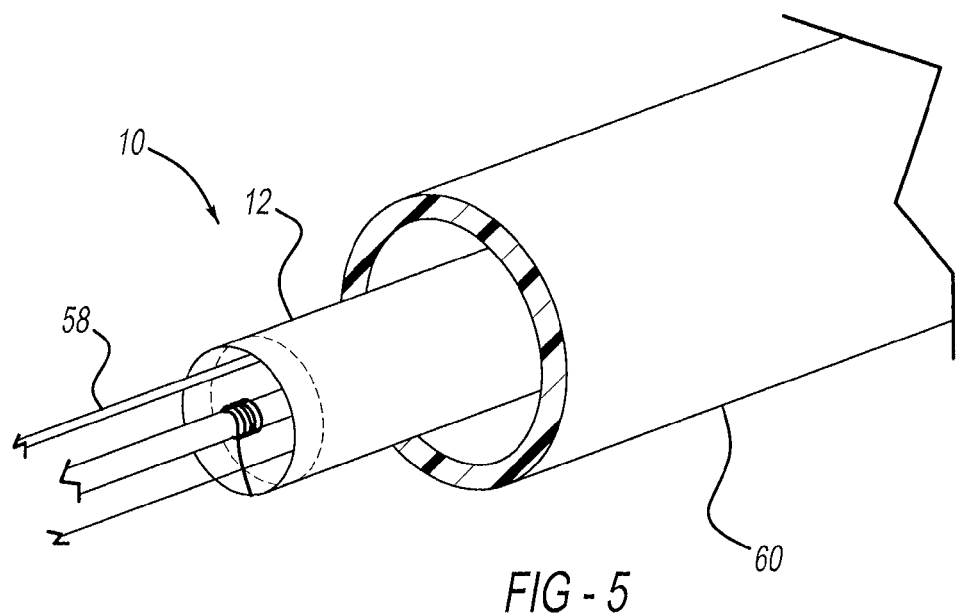
FIG. 5 is an isometric view illustrating the stent graft within a catheter for delivery to a patient's vasculature.

With reference to FIG. 5, the graft 12 described above can be compressed into a delivery state, with the cannula 22 rotated to wind the suture 26 therearound so that the stent graft 12 has a reduced diameter. The reduced diameter graft 12 can be inserted into a catheter 60 or similar tubular intravenous delivery device. The catheter 60 having the stent graft 12 therein can then be threaded over the guide wire 58 as known in the art for translation along the guide wire 58 into the patient's body and ultimately to the target site.

In one form, the graft 12 can be attached at its proximal and distal ends to the catheter 60 via attachments (not shown) that hold the rotary position of the graft in a generally fixed position relative to the catheter 60. The attachments could be released using a trigger wire (not shown) or other known method. Additionally or alternatively, the catheter 60 can also include a sheath portion (not shown) that can assist in constraining the diameter of the graft 12 during delivery and be withdrawn similar to the catheter 60, which is described below.

The catheter 60 is advanced over the guide wire 58 toward the target site using known procedures. Once the catheter 60 has arrived at the target site, the catheter 60 can be withdrawn, exposing the graft 12 to the vasculature.

In this state, the graft 12 will remain in its compressed condition, even if it is a self-expanding type, because the suture 26 has been wound around the cannula 22, which can remain in place after the catheter 60 is withdrawn.

The cannula 22 can be rotated to allow the suture 26 to unwind. The stent graft will be allowed to expand, either due to the built up potential energy in the self-expanding style, or through balloon expansion. The surgeon can monitor the positioning of the graft 12 during its expansion.

Figure 6:
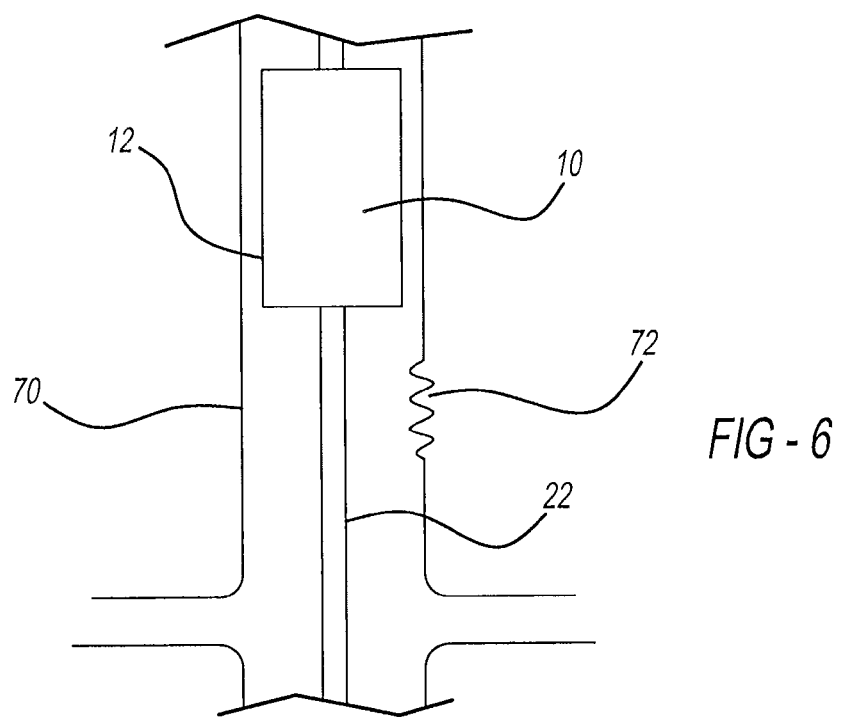
FIGS. 6-8 are schematic views illustrating the stent graft in various delivery states.
Figure 7:
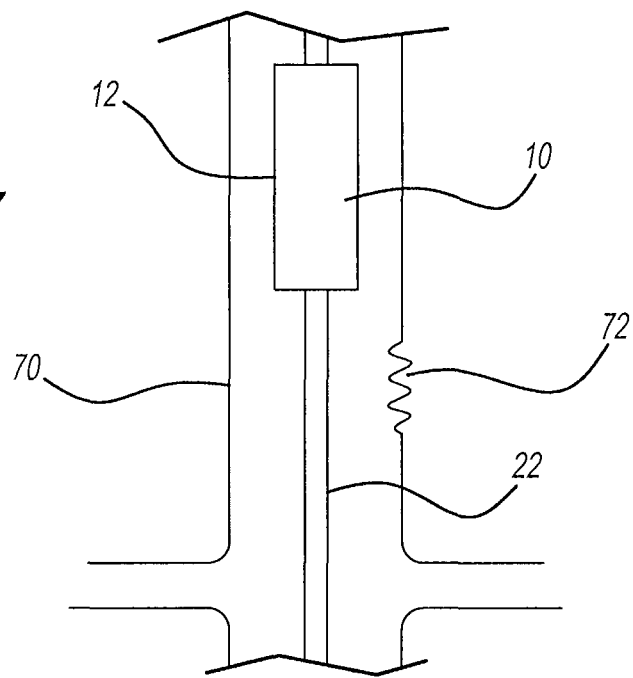
Figure 8:
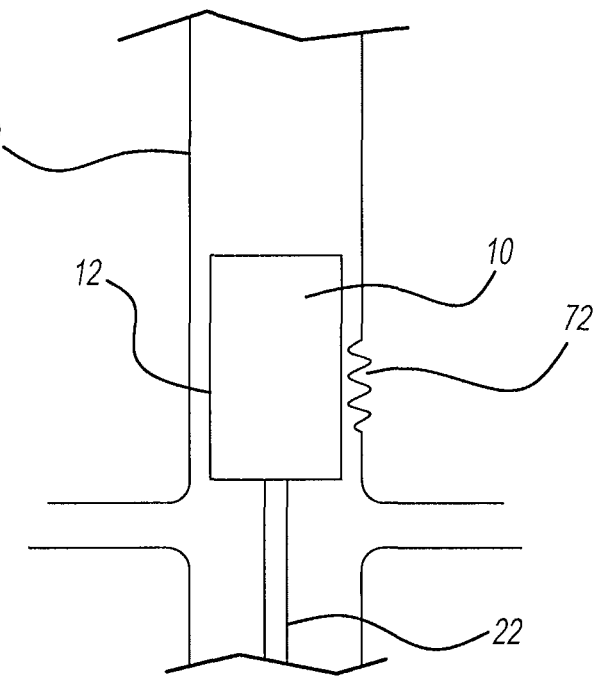

With reference to FIGS. 6-8, the graft 12 can expand to engage the anatomical wall 70 at the location of the anatomical defect 72 to allow for blood to flow through the graft 12 and to allow for the defect to heal itself, if possible.

The surgeon can determine whether the graft 12 is in the proper location after at least partial expansion. If the surgeon wishes to re-position the graft 12, the surgeon can rotate the cannula 22 in the opposite direction to wind the suture 26, which causes the diameter of the stent graft 12 to become reduced (FIG. 7), allowing for the stent graft 12 to be moved to a different location. The graft 12 will remain at its reduced diameter until the surgeon wishes to allow it to expand again. To allow the graft 12 to expand again, the cannula 22 can be rotated to allow the suture to unwind and the stent 10 can expand (FIG. 8).

This process of alternating expansion and compression can be repeated multiple times until the surgeon is satisfied with the location of the expanded stent 10. Until the suture 26 is released, the surgeon has the ability to repeatedly wind and unwind the suture 26 to compress and expand the graft 12.

Once the surgeon is satisfied with the location of the graft 12, the surgeon can release the suture from the cannula 22, as described above, depending on the attachment member 24 used to secure the suture 26 to the cannula 22. If the attachment member 24 is in the form of the hook 40, the surgeon can rotate the cannula 22 in the direction to unwind the suture 26 and continue rotating the cannula 22 so that the curved shape of the hook 40 cams along the loop 44 of the suture, causing the hook 40 to retract out of the loop 44 and freeing the suture 26 from the cannula 22.

If the attachment member 24 is in the form of a trigger wire 46, the surgeon can withdraw the trigger wire 46 away from the graft 12, causing the trigger wire 46 to be pulled through and out of engagement with the loop 44 of the suture 26.

Once the suture 26 has been released from the cannula 22, the cannula 22 can be withdrawn from the graft 12, leaving the graft 12 in place in the patient's body for treating the anatomical defect 72. The surgeon can further remove other elements related to the delivery of the graft 12, such as the guide wire 58, in a manner known in the art.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

What is claimed is:

1. A system for deploying an endoluminal prosthesis, the system comprising:
    a graft comprising biocompatible material having at least one lumen extending therethrough;
    a rotatable cannula extending at least partially through the graft lumen, the cannula being rotatable relative to the graft; and
    a suture having a first portion and a second portion, the first portion being coupled to the rotatable cannula within the graft lumen and windable around the cannula and the second portion being coupled to the graft, wherein an extent to which the suture is wound around the cannula adjusts in response to rotation of the rotatable cannula and an extent to which the suture is coupled to the graft correspondingly adjusts to vary a diameter of the graft.

2. The system of claim 1 wherein the graft has a first diameter in response to rotation of the cannula in a first direction, the graft has a second diameter larger than the first diameter in response to additional rotation of the cannula in the first direction, and the graft has a third diameter less than the second diameter in response to rotation of the cannula in a direction opposite the first direction.

3. The system of claim 1 wherein the suture is at least partially wound around the cannula at the location within the graft lumen.

4. The system of claim 1 wherein the graft comprises a plurality of openings therethrough, the suture first portion is at least partially threaded through the plurality of openings, and alternating portions of the suture first portion are disposed inside and outside of the graft.

5. The system of claim 1 wherein the suture includes a loop portion at a first end thereof, the cannula has an attachment member at the location within the lumen where the first portion of the suture is coupled to the cannula, and the loop portion of the suture is coupled to the attachment member to couple the first portion of the suture to the cannula.

6. The system of claim 5 wherein the attachment member comprises a hook protruding radially from the cannula.

7. The system of claim 5 wherein the attachment member comprises a wire extending longitudinally along the cannula.

8. A method for delivering the endoluminal prosthesis system of claim 1, the method comprising the steps of:
locating, within a patient's body, the endoluminal prosthesis, wherein the suture is at least partially wound about the rotatable cannula and at least partially mounted about a perimeter of the graft;
rotating the cannula in a first direction;
in response to rotating the cannula in the first direction, unwinding a portion of the suture;
expanding the graft outwardly;
rotating the cannula in a second direction that is opposite the first direction;
in response to rotating the cannula in the second direction, winding a portion of the suture about the cannula; and
reducing the diameter of the graft.

9. The method of claim 8, wherein the graft includes a plurality of laterally spaced openings in the graft, the suture extends about the graft through the openings in an alternating fashion, a first portion of the suture extending about the graft is outside the graft, and a second portion of the suture extending about the graft is inside the graft.

10. The method of claim 8, wherein the cannula includes an attachment member and an inner end of the suture is releasably mounted to the attachment member.

11. The method of claim 10, wherein the inner end of the suture includes a loop portion and the attachment member extends through the loop portion.

12. The method of claim 11, wherein the attachment member comprises a hook fixedly mounted to the cannula.

13. The method of claim 12 further comprising further rotating the cannula in the first direction and releasing the inner end of the suture from the hook.

14. The method of claim 11, wherein the attachment member comprises a wire extending along the cannula and through the loop portion.

15. The method of claim 14 further comprising withdrawing the wire away from the suture and out of engagement with the loop portion.

16. The method of claim 14 wherein the cannula includes a lumen extending therealong, the cannula includes a pair of longitudinally aligned openings through a surface of the cannula, and the wire extends within the cannula lumen through one of the openings to the outside of the cannula through the other opening to the cannula lumen, an intermediate portion of the wire is outside the cannula, and the intermediate portion extends through the suture loop.

17. A system for deploying an endoluminal prosthesis, the system comprising:
a graft comprising biocompatible material having at least one lumen extending therethrough;
a rotatable cannula extending at least partially through the graft lumen; and
a suture having a first portion and a second portion, the first portion being coupled to the rotatable cannula within the graft lumen and the second portion being coupled to the graft, wherein the lengths of the first and second portions adjust in response to rotation of the rotatable cannula to vary a diameter of the graft;
wherein the suture includes a loop portion at the first end thereof, the cannula has an attachment member thereof, and the loop portion is coupled to the attachment member;
wherein the attachment member comprises a wire extending longitudinally along the cannula;
wherein the cannula has a tubular body with a lumen extending therethrough and first and second longitudinally spaced openings in the body, the wire extends through the lumen, through the first opening, and through second opening, an intermediate portion of the wire is disposed outside the cannula, and the intermediate portion extends through the suture loop.

18. A system for deploying an endoluminal prosthesis, the system comprising:
a graft comprising biocompatible material having at least one lumen extending therethrough;
a rotatable cannula extending at least partially through the graft lumen, the rotatable cannula being rotatable relative to the graft; and
a suture having a first portion and a second portion, the first portion being wound around the rotatable cannula at a location within the graft lumen and the second portion extending along the perimeter of the graft, wherein, in response to rotation of the rotatable cannula relative to the graft, an extent to which the first portion is wound around the cannula adjusts and an extent to which the second portion extends along the perimeter correspondingly adjusts to vary diameter of the graft.

19. The system of claim 18 further comprising a stent coupled to the graft.

20. The system of claim 19, wherein the stent comprises a self-expanding stent.

* * * * *